(12) United States Patent
Struthers et al.

(10) Patent No.: US 12,064,613 B2
(45) Date of Patent: Aug. 20, 2024

(54) CIRCULATORY SUPPORT PUMP CENTERING ANCHORING AND CENTERING DEVICE

(71) Applicant: Boston Scientific Scimed Inc., Maple Grove, MN (US)

(72) Inventors: Brett C. Struthers, Victoria, MN (US); Thomas P. Jancaric, Maple Grove, MN (US); Paul F. Chouinard, Maple Grove, MN (US); Umang Anand, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/980,026

(22) Filed: Nov. 3, 2022

(65) Prior Publication Data

US 2023/0051191 A1     Feb. 16, 2023

Related U.S. Application Data

(63) Continuation of application No. 16/997,448, filed on Aug. 19, 2020, now Pat. No. 11,517,737.

(Continued)

(51) Int. Cl.
*A61M 60/148* (2021.01)
*A61B 17/34* (2006.01)

(52) U.S. Cl.
CPC ....... *A61M 60/148* (2021.01); *A61B 17/3468* (2013.01); *A61M 2205/0266* (2013.01)

(58) Field of Classification Search
CPC ...... A61B 17/3468; A61M 2205/0266; A61M 60/13; A61M 60/148; A61M 60/237; A61M 60/857; A61M 60/861; A61M 60/865
See application file for complete search history.

(56) References Cited

U.S. PATENT DOCUMENTS 8,690,749 B1   4/2014  Nunez
11,517,737 B2 * 12/2022 Struthers ............. A61M 60/237
(Continued)

FOREIGN PATENT DOCUMENTS

WO    2018/129177 A1    7/2018

OTHER PUBLICATIONS

International Search Report and and Written Opinion received for International patent application No. PCT/US2020/046989, mailed on Nov. 18, 2020, 18 pages.

*Primary Examiner* — Jon Eric C Morales
(74) *Attorney, Agent, or Firm* — Seager, Tufte & Wickhem LLP

(57) ABSTRACT

Embodiments in the present disclosure relate to an anchoring and centering device for a circulatory support pump. An exemplary apparatus comprises an expandable anchoring device extending along a longitudinal axis, wherein the expandable anchoring device is arranged about a central axis. A distal portion of the expandable anchoring device defines an annulus through which the cardiac pump can be arranged and to which the cardiac pump can be releasable coupled. A proximal portion of the expandable anchoring device is configured to circumferentially expand to an unconstrained configuration that has a cross-sectional diameter greater than a diameter of the annulus. The exemplary apparatus also includes a constraining member arranged over the expandable anchoring device to constrain the expandable anchoring device in a constrained configuration for delivery of the anchoring apparatus.

15 Claims, 12 Drawing Sheets

Related U.S. Application Data

(60) Provisional application No. 62/889,674, filed on Aug. 21, 2019.

(56) References Cited

U.S. PATENT DOCUMENTS

| | | |
|---|---|---|
| 2010/0191035 A1 | 7/2010 | Kang |
| 2010/0249489 A1 | 9/2010 | Jarvik |
| 2015/0258260 A1* | 9/2015 | Tuseth ................ A61M 60/861 |
| | | 600/16 |
| 2017/0232170 A1 | 8/2017 | Jarvik |
| 2018/0339092 A1 | 11/2018 | Larose |
| 2020/0139032 A1* | 5/2020 | Bryson ............... A61M 60/508 |

* cited by examiner

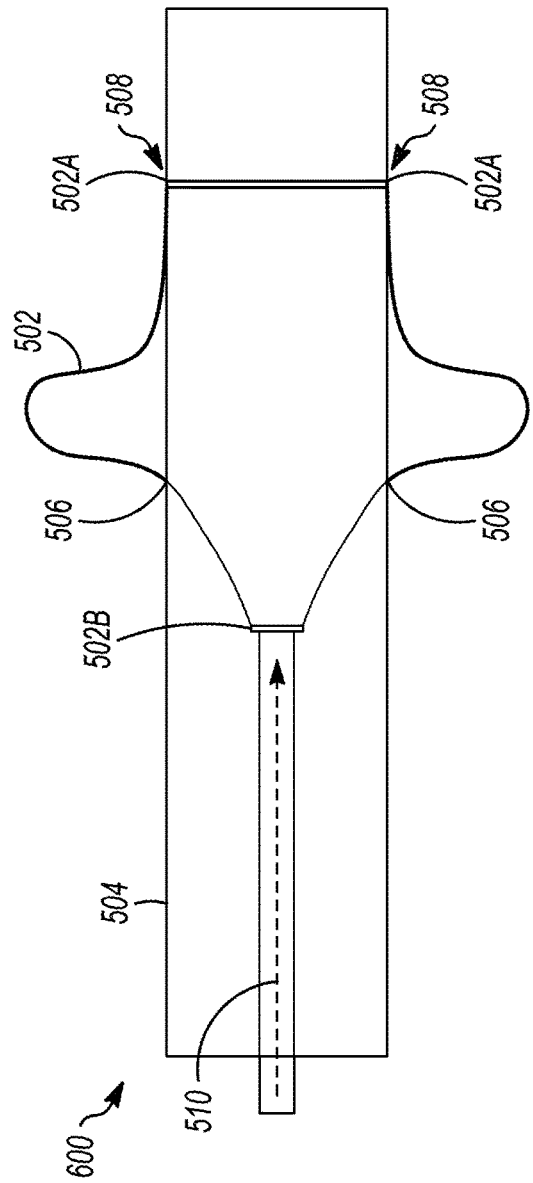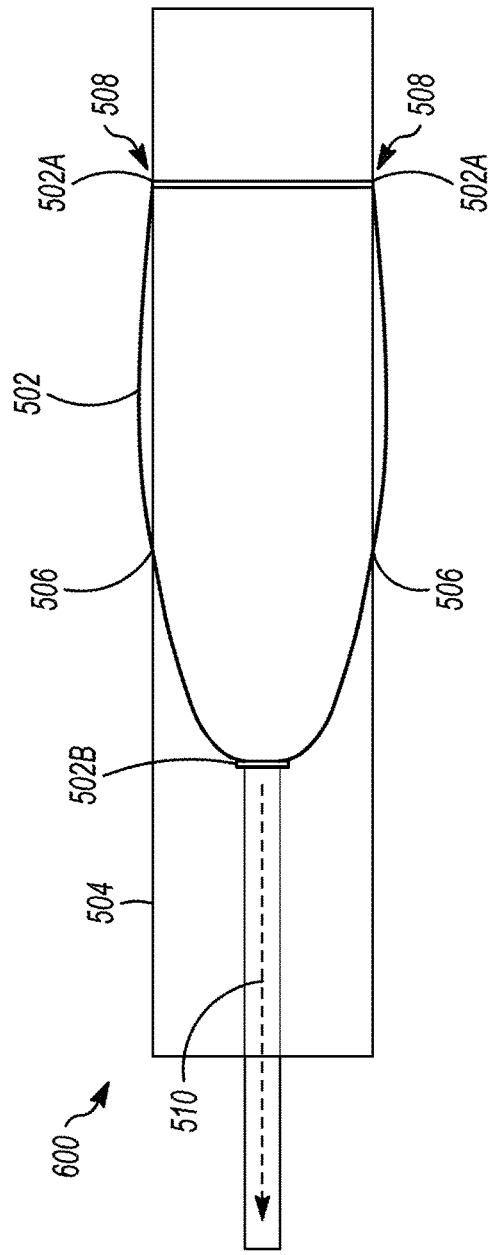

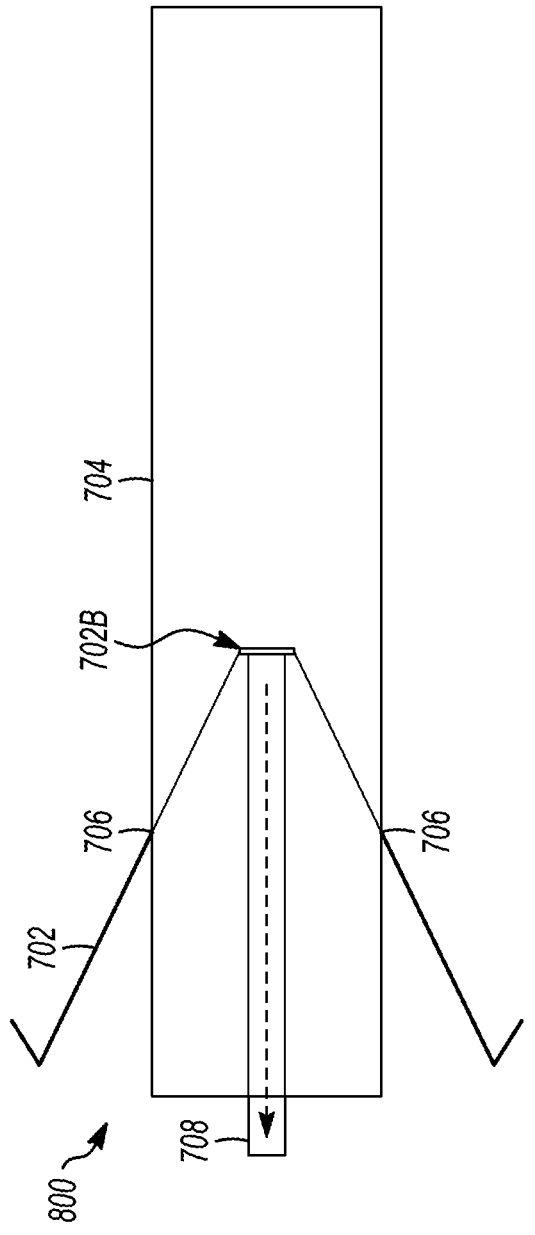
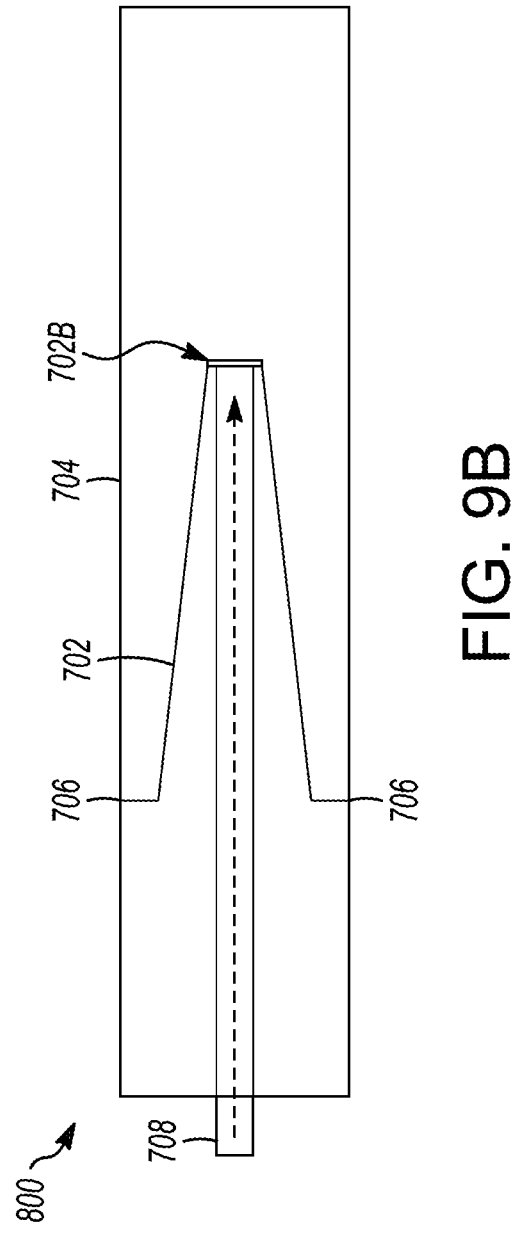

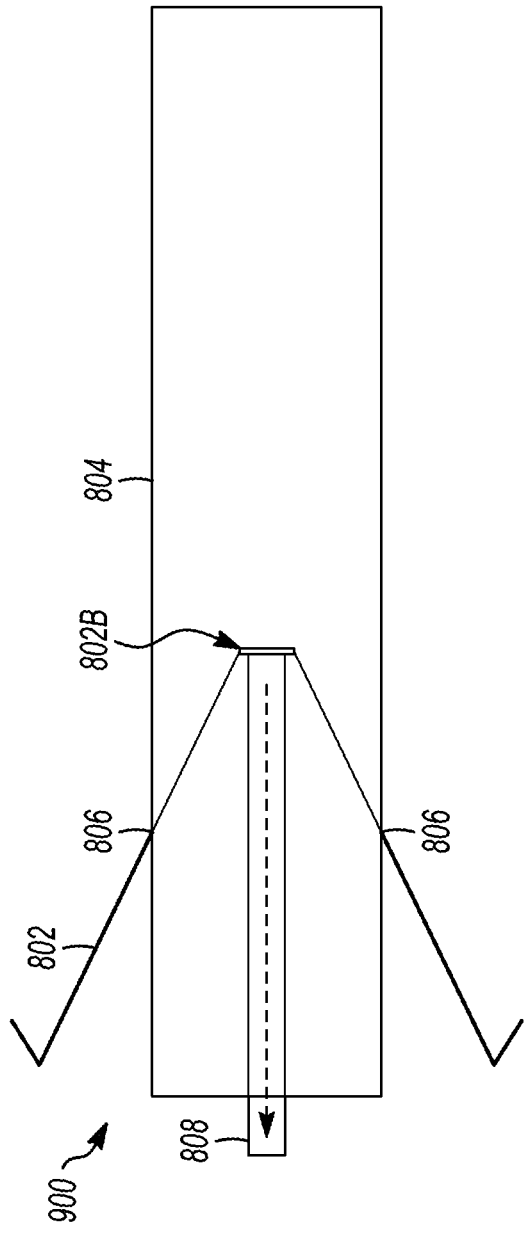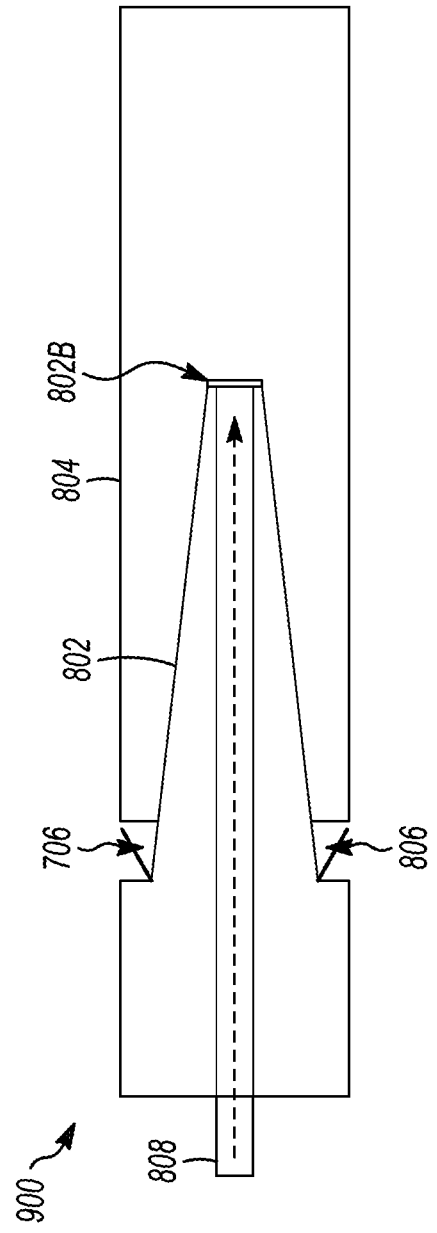

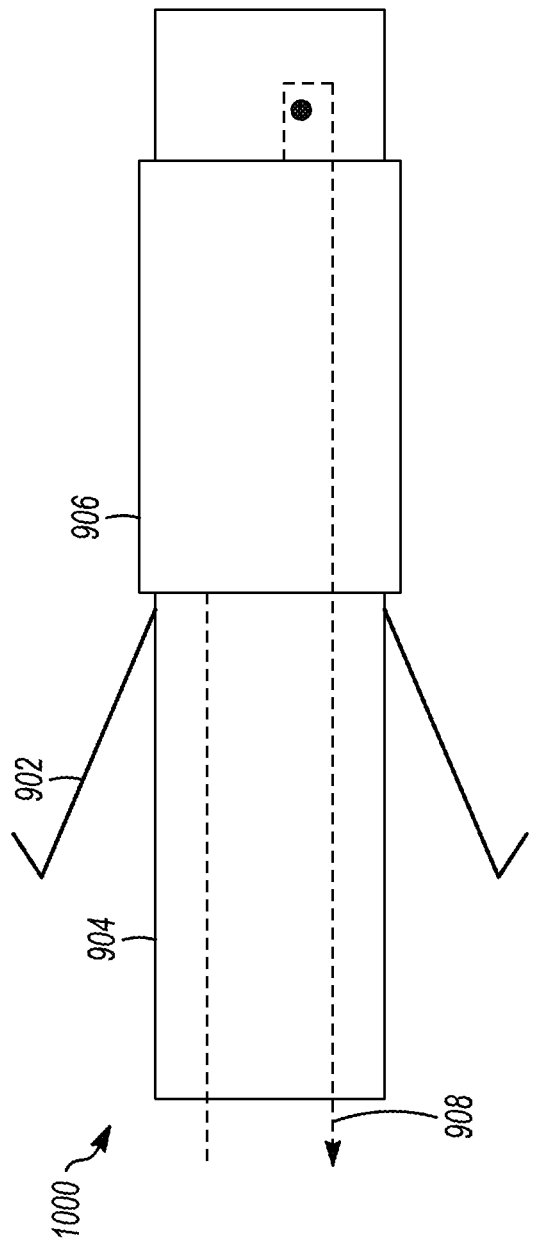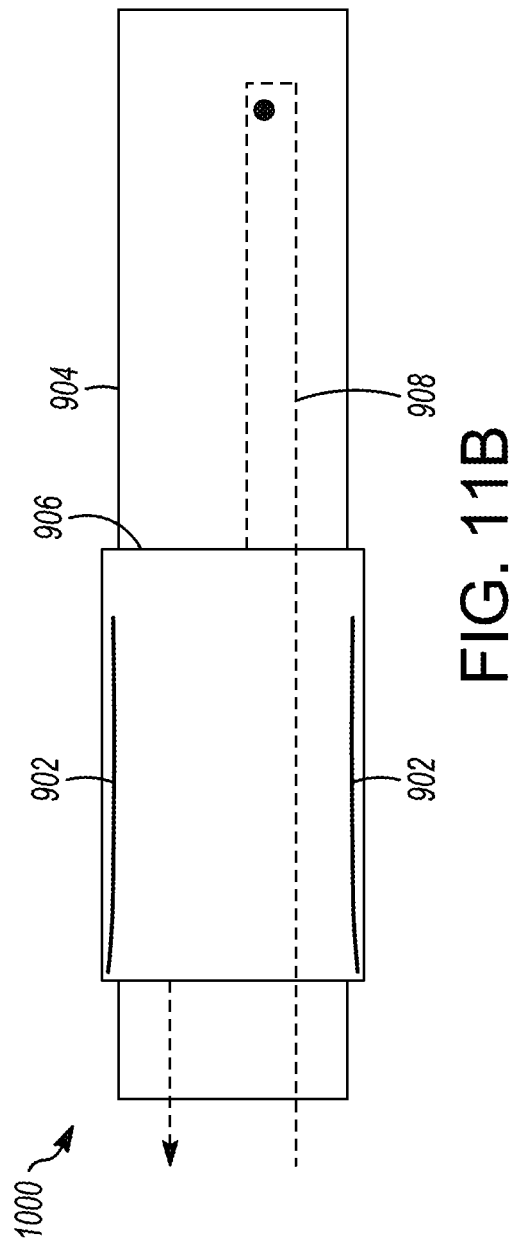

US 12,064,613 B2

CIRCULATORY SUPPORT PUMP CENTERING ANCHORING AND CENTERING DEVICE

CROSS REFERENCE TO RELATED APPLICATION

This application is a continuation application of and claims priority to U.S. Ser. No. 16/997,448, filed Aug. 19, 2020, which claims priority to Provisional Application No. 62/889,674, filed Aug. 21, 2019, which are herein incorporated by reference in their entirety.

TECHNICAL FIELD

The present disclosure relates to percutaneous circulatory support devices. More specifically, the disclosure relates to an anchoring and centering device for a circulatory support pump.

BACKGROUND

Circulatory support devices are devices that support the pumping action of the heart. These devices may be disposed through a valve opening such as, for example, an aortic valve. Typical circulatory support devices are prone to moving, resulting in a need for repositioning before treatment is continued.

SUMMARY

Embodiments disclosed herein relate to anchoring and centering devices for a circulatory support pump. Exemplary embodiments include, but are not limited to, the following examples.

In an Example 1, an anchoring apparatus for centering a cardiac pump, comprises: an expandable anchoring device extending along a longitudinal axis, wherein the expandable anchoring device is arranged about a central axis, wherein a distal portion of the expandable anchoring device defines an annulus through which the cardiac pump can be arranged and to which the cardiac pump can be releasable coupled, and wherein a proximal portion of the expandable anchoring device is configured to circumferentially expand to an unconstrained configuration that has a cross-sectional diameter greater than a diameter of the annulus; and a constraining member arranged over the expandable anchoring device to constrain the expandable anchoring device in a constrained configuration for delivery of the anchoring apparatus.

In an Example 2, the apparatus of Example 1, wherein the proximal portion has a conical shape.

In an Example 3, the apparatus of any one of Examples 1 or 2, wherein the proximal portion comprises a plurality of proximal portions that are configured to expand equidistant from the central axis when in the unconstrained configuration.

In an Example 4, the apparatus of Example 3, wherein the plurality of proximal portions comprise a plurality of separate, elongate members.

In an Example 5, the apparatus of Example 4, wherein the plurality of separate, elongate members are barbs.

In an Example 6, the apparatus of any one of Examples 3-5, wherein the plurality of proximal portions comprises a plurality of loop elements.

In an Example 7, the apparatus of any one of Examples 1-6, wherein the distal portion includes an elongate member that is secured to a coupling loop of the cardiac pump via an interference fit.

In an Example 8, the apparatus of any one of Examples 1-7, wherein the distal portion comprises portions that are overlapping when in the constrained configuration and are non-overlapping when in the unconstrained configuration.

In an Example 9, the apparatus of any one of Examples 1-8, further comprising a delivery catheter, wherein the delivery catheter has a tricuspid cross-sectional shape, and wherein the anchoring apparatus is arranged over the delivery catheter during delivery of the anchoring apparatus.

In an Example 10, the apparatus of any one of Examples 1-9, wherein the plurality of expandable anchoring devices are formed from nitinol.

In an Example 11, a method for delivering an anchoring apparatus for centering a cardiac pump, the method comprising: arranging the anchoring apparatus over or within a delivery catheter, the anchoring apparatus comprising: an expandable anchoring device extending along a longitudinal axis, wherein the expandable anchoring device is arranged about a central axis, wherein a distal portion of the expandable anchoring device defines an annulus through which the cardiac pump can be arranged and to which the cardiac pump can be releasable coupled, and wherein a proximal portion of the expandable anchoring device is configured to circumferentially expand to an unconstrained configuration that has a cross-sectional diameter greater than a diameter of the annulus; and a constraining member arranged over the expandable anchoring device to constrain the expandable anchoring device in a constrained configuration for delivery of the anchoring apparatus; advancing the apparatus over the cardiac pump arranged within a subject's heart; releasably coupling the anchoring apparatus to the cardiac pump; and actuating the anchoring apparatus from its constrained configuration.

In an Example 12, the method of Example 11, wherein the anchoring apparatus further comprises an actuation member, wherein the constraining member is a sheath arranged around the proximal portion that comprises at least one aperture, and wherein actuating the anchoring apparatus comprises actuating the actuation member so the anchoring apparatus projects through the at least one aperture of the sheath.

In an Example 13, the method of Example 11, wherein the constraining member is a sheath arranged around the proximal portion, and wherein actuating the anchoring apparatus comprises translating the sheath so that it is no longer arranged around the proximal portion.

In an Example 14, the method of any one of Examples 11-13, wherein the distal portion includes an elongate member that is secured to a coupling loop of the cardiac pump via an interference fit, and wherein releasably coupling the anchoring apparatus to the cardiac pump comprises inserting the elongate member through the coupling loop.

In an Example 15, the method of any one of Examples 11-14, further comprising removing the anchoring apparatus by arranging the constraining member over the expandable anchoring device and withdrawing the anchoring apparatus.

In an Example 16, an anchoring apparatus for centering a cardiac pump, comprises: an expandable anchoring device extending along a longitudinal axis, wherein the expandable anchoring device is arranged about a central axis, wherein a distal portion of the expandable anchoring device defines an annulus through which the cardiac pump can be arranged and to which the cardiac pump can be releasable coupled, and wherein a proximal portion of the expandable anchoring device is configured to circumferentially expand to an unconstrained configuration that has a cross-sectional diameter greater than a diameter of the annulus; and a constraining member arranged over the expandable anchoring device to constrain the expandable anchoring device in a constrained configuration for delivery of the anchoring apparatus.

In an Example 17, the apparatus of Example 16, wherein the proximal portion has a conical shape.

In an Example 18, the apparatus of Example 16, wherein the cross-sectional shape of the proximal portion is a disk.

In an Example 19, the apparatus of Example 16, wherein the proximal portion comprises a plurality of proximal portions that are configured to expand equidistant from the central axis when in the unconstrained configuration.

In an Example 20, the apparatus of Example 19, wherein the plurality of proximal portions comprise a plurality of separate, elongate members.

In an Example 21, the apparatus of Example 20, wherein the plurality of separate, elongate members are barbs.

In an Example 22, the apparatus of Example 19, wherein the plurality of proximal portions comprises a plurality of loop elements.

In an Example 23, the apparatus of Example 16, wherein the distal portion includes an elongate member that is secured to a coupling loop of the cardiac pump via an interference fit In an Example 24, the apparatus of Example 16, wherein the distal portion comprises overlapping portions when in the constrained configuration and are non-overlapping when in the unconstrained configuration.

In an Example 25, the apparatus of Example 16, further comprising a delivery catheter, wherein the delivery catheter has a tricuspid cross-sectional shape, and wherein the anchoring apparatus is arranged over the delivery catheter during delivery of the anchoring apparatus.

In an Example 26, the apparatus of Example 16, wherein the plurality of expandable anchoring devices are formed from nitinol.

In an Example 27, a method for delivering an anchoring apparatus for centering a cardiac pump, the method comprises: arranging the anchoring apparatus over or within a delivery catheter, the anchoring apparatus comprising: an expandable anchoring device extending along a longitudinal axis, wherein the expandable anchoring device is arranged about a central axis, wherein a distal portion of the expandable anchoring device defines an annulus through which the cardiac pump can be arranged and to which the cardiac pump can be releasable coupled, and wherein a proximal portion of the expandable anchoring device is configured to circumferentially expand to an unconstrained configuration that has a cross-sectional diameter greater than a diameter of the annulus; and a constraining member arranged over the expandable anchoring device to constrain the expandable anchoring device in a constrained configuration for delivery of the anchoring apparatus; advancing the apparatus over the cardiac pump arranged within a subject's heart; releasably coupling the anchoring apparatus to the cardiac pump; and actuating the anchoring apparatus from its constrained configuration.

In an Example 28, the method of Example 27, wherein the anchoring apparatus further comprises an actuation member, wherein the constraining member is a sheath arranged around the proximal portion that comprises at least one aperture, and wherein actuating the anchoring apparatus comprises actuating the actuation member so the anchoring apparatus projects through the at least one aperture of the sheath.

In an Example 29, the method of Example 27, wherein the constraining member is a sheath arranged around the proximal portion, and wherein actuating the anchoring apparatus comprises translating the sheath so that it is no longer arranged around the proximal portion.

In an Example 30, the method of Example 27, wherein the distal portion includes an elongate member that is secured to a coupling loop of the cardiac pump via an interference fit, and wherein releasably coupling the anchoring apparatus to the cardiac pump comprises inserting the elongate member through the coupling loop.

In an Example 31, the method of Example 27, further comprising removing the anchoring apparatus by arranging the constraining member over the expandable anchoring device and withdrawing the anchoring apparatus.

In an Example 32, the method of Example 27, wherein the proximal portion has a conical shape.

In an Example 33, the method of Example 27, wherein the distal portion comprises portions that are overlapping when in the constrained configuration and are non-overlapping when in the unconstrained configuration.

In an Example 34, the method of Example 27, wherein the proximal portion comprises a plurality of proximal portions that are configured to expand equidistant from the central axis when in the unconstrained configuration.

In an Example 35, the method of Example 33, wherein the plurality of proximal portions comprise a plurality of separate, elongate members.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

FIGS. 7A and 7B are schematic diagrams depicting operation of an exemplary anchoring deployment mechanism, in accordance with embodiments of the subject matter disclosed herein.

FIGS. 9A and 9B are schematic diagrams depicting operation of another exemplary anchoring deployment mechanism, in accordance with embodiments of the subject matter disclosed herein.

FIGS. 10A and 10B are schematic diagrams depicting operation of another exemplary anchoring deployment mechanism, in accordance with embodiments of the subject matter disclosed herein.

FIGS. 11A and 11B are schematic diagrams depicting operation of another exemplary anchoring deployment mechanism, in accordance with embodiments of the subject matter disclosed herein.

Figure 1:
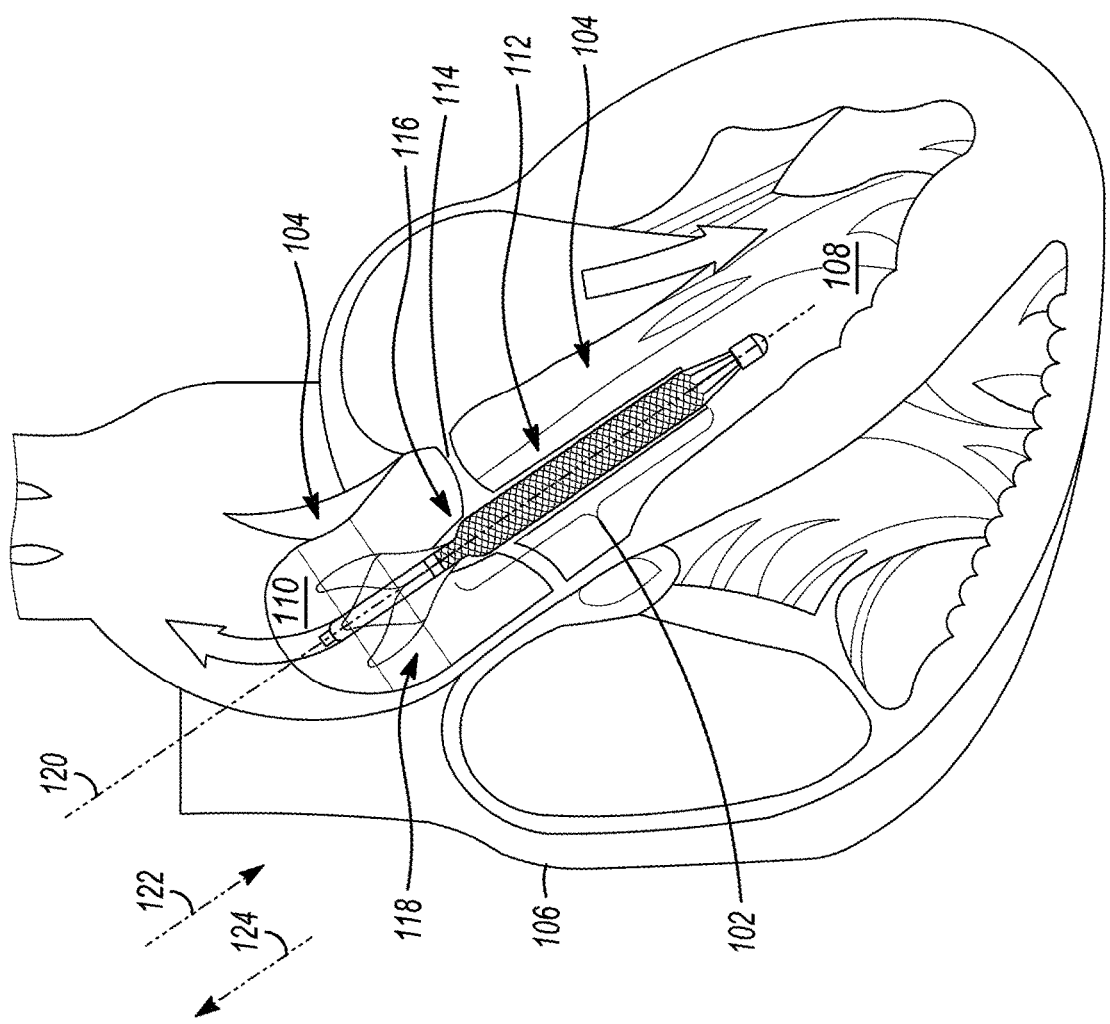
FIG. 1 depicts a conceptual diagram of a circulatory support device having an exemplary anchoring device anchored within a heart, in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

DETAILED DESCRIPTION

Embodiments disclosed herein include a circulatory support device having an anchoring device configured to be employed with a heart. The anchoring device may be configured to prevent inadvertent migration of the circulatory support device from an exemplary location during operation of the circulatory support device. For example, the anchoring device may be configured to reduce the likelihood of translation of the circulatory support device into or out of the aorta. As another example, the anchoring device may be configured to center the circulatory support device within the aortic valve to prevent the circulatory support device from being biased toward the perimeter of the aortic valve resulting in aortic regurgitation. Centering of the circulatory support device may also have the added benefit of mitigating abrasion to the aortic valve leaflets by the circulatory support device. Furthermore, by reducing the likelihood of device contact with the annulus of the aortic valve, the probability of disrupting calcification from the aortic valve resulting in embolization is reduced, which reduces the risk of stroke or other organ damage. A centered device is also less likely to engage the mitral valve elements such as the papillary heads or chordae tendineae. Another advantage of a centered device is the likelihood of contact with the left ventricle walls is reduced, especially the septal wall which might result in ectopic beats.

FIG. 1 depicts a conceptual diagram of a circulatory support device 102 having an exemplary anchoring device 104 anchored within a heart 106, in accordance with embodiments of the subject matter disclosed herein. According to embodiments, the circulatory support device 102 may be a ventricular assist device, such as a pump, that is configured to pump blood from a left ventricle 108 of a subject into the subject's aorta 110. More specifically, a distal portion 112 of the circulatory support device 102 is arranged in the left ventricle 108. The circulatory support device 102 extends through the aortic valve 114 so that a proximal portion 116 extends into the aorta 110. During operation, the circulatory support device 102 draws blood from the left ventricle 108, through a cannula 118 of the circulatory support device 102 and is released into the aorta 110. Additionally, or alternatively, the circulatory support device 102 may be used to facilitate pumping blood from some other aspect of the subject's heart and/or vasculature into an adjacent portion of the heart and/or vasculature.

The longitudinal, central axis 120 bisects the aortic valve 114. In exemplary embodiments, the cannula 118 of the circulatory support device 102 is centered and extends along the longitudinal, central axis 120 so that the circulatory support device 102 is centered in the aortic valve 114. In the event the circulatory support device 102 is not centered within the aortic valve 114, the circulatory support device 102 may prevent the aortic valve 114 from closing, resulting in aortic regurgitation (i.e., where blood flows backward from the aorta 110 to left ventricle 108). Such positioning can also damage the leaflets of the aortic valve 114. Furthermore, in exemplary embodiments, the circulatory support device 102 should not translate in a distal direction 122 or a proximal direction 124. Otherwise, the circulatory support device 102 may project farther into the left ventricle 108 or the aorta 110 than intended, reducing and/or eliminating the usefulness of the circulatory support device 102. Conventional embodiments do not adequately address these problems. The embodiments disclosed herein, however, provide a solution to these problems by including an anchoring device 104 releasably coupled to the circulatory support device 102 such that the anchoring device 104 anchors to the heart 102 to prevent translational movement of the circulatory support device 102 and/or radial movement of the circulatory support device 102, as described in more detail below.

The illustrative system shown in FIG. 1 is not intended to suggest any limitation as to the scope of use or functionality of embodiments of the present disclosure. The system also should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2:
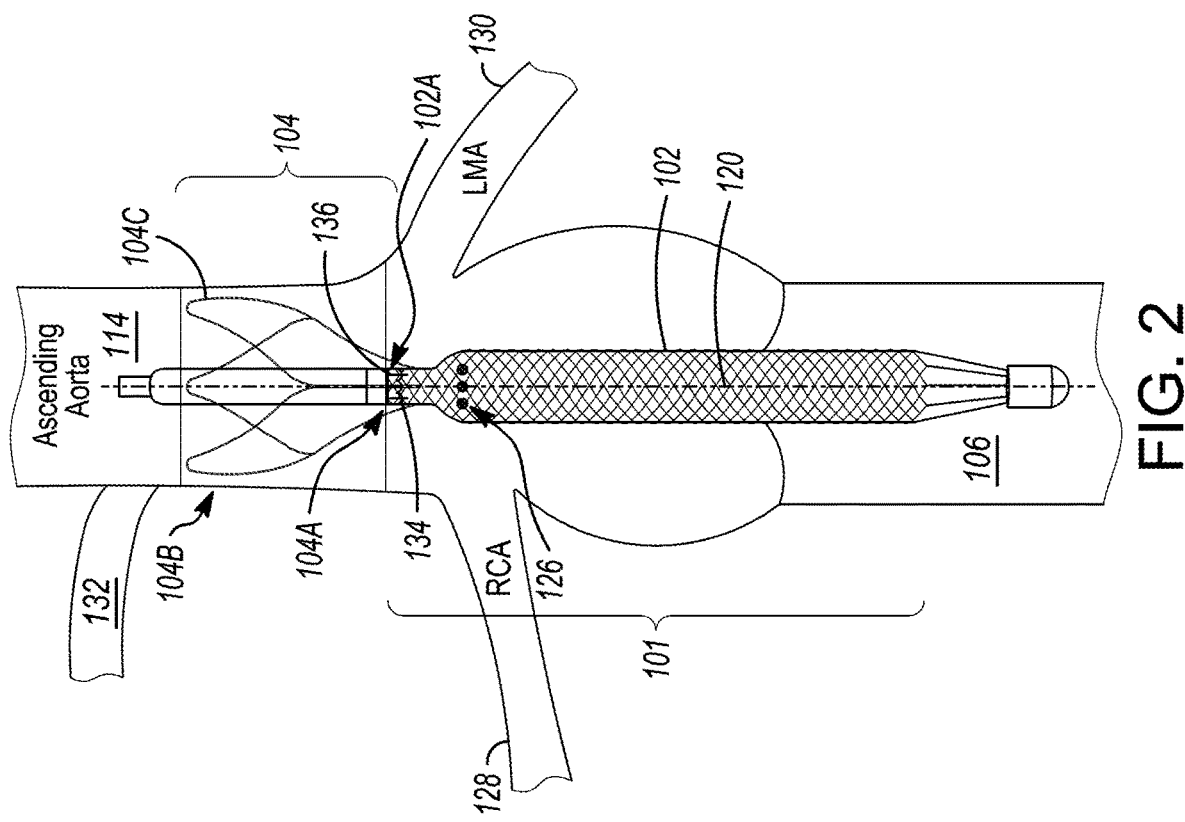
FIG. 2 depicts a conceptual diagram of an exemplary implantation location of a circulatory support device having an exemplary anchoring device, in accordance with embodiments of the subject matter disclosed herein.

FIG. 2 depicts a conceptual diagram of an exemplary implantation location of a circulatory support device 102 having an exemplary anchoring device 104, in accordance with embodiments of the subject matter disclosed herein. In exemplary embodiments, the circulatory support device 102 should be positioned so that the outflow windows 126 of the circulatory support device 102 are approximately 10 millimeters (mm) proximal the right coronary artery (RCA) 128 and left main artery (LMA) 130 to facilitate efficient blood flow out of the circulatory support device 102 into the aorta 110. In exemplary embodiments, the outflow windows 126 of the circulatory support device 102 should also not be positioned over the brachiocephalic artery 132. Instead, the outflow windows 126 should be positioned 10 mm distal to the brachiocephalic artery 132.

In embodiments, the anchoring device 104 facilitates maintaining the circulatory support device 102 in the exemplary position described above. For example, the circulatory support device 102 may be positioned in the exemplary position described above. After or during the positioning of the circulatory support device 102, the anchoring device 104 may be delivered, in a constrained configuration, over or within a delivery catheter (not shown) so the distal portion 104A is arranged over a proximal portion 102A of the circulatory support device 102. In embodiments, elements of the distal portion 104A may define an annulus (see, e.g., FIG. 4B) through which the circulatory support device 102 can be received. To maintain the anchoring device 104 in a constrained state, a constraining member (not shown) may be arranged around the anchoring device 104. The constraining member be a sleeve, a sheath, a catheter, and/or the like. Exemplary constraining members are described in more detail below in relation to FIGS. 7A-13B.

In embodiments, the distal portion 104A of the anchoring device 104 may be releasably coupled to the proximal portion 102A of the circulatory support device 102. To do so, the proximal portion 102A may include loop elements 134 through which elongate members 136 of the anchoring device 104 are inserted. As stated above, the elongate members 136 may define an annulus (see, e.g., FIG. 4B) through which the anchoring device 104 can be arranged. In embodiments, the loop elements 134 and the elongate members 136 may form an interference fit to prevent inadvertent detachment of the elongate members 136 by the loop elements 134.

Either before or after coupling the distal portion 104A to the proximal portion 102A, the constraining member may be removed from the anchoring device 104 so the anchoring device 104 can circumferentially expand to an unconstrained state (as shown). In the unconstrained state, the anchoring device 104 may include a proximal portion 104B that expands to have a cross section diameter that is larger than the diameter defined by the annulus of the distal portion 104A. As such, edges 104C of the proximal portion 104B expand so the edges 104C contact and abut the walls of the aorta 114. Due to the contact between the anchoring device 104 and the walls of the aorta 114, the anchoring device 104 anchors the circulatory support device 102 to the heart 106. In embodiments, the anchoring device 104 may allow for blood to freely pass along the outside of the circulatory support device 102. In embodiments, the anchoring device 104 may expand to have a conical shape as shown. In embodiments, the anchoring device 104 may be formed from nitinol. Additional exemplary embodiments of anchoring devices are described below in relation to FIGS. 3-5B.

The illustration shown in FIG. 2 is not intended to suggest any limitation as to the scope of use or functionality of embodiments of the present disclosure. The illustration also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3:
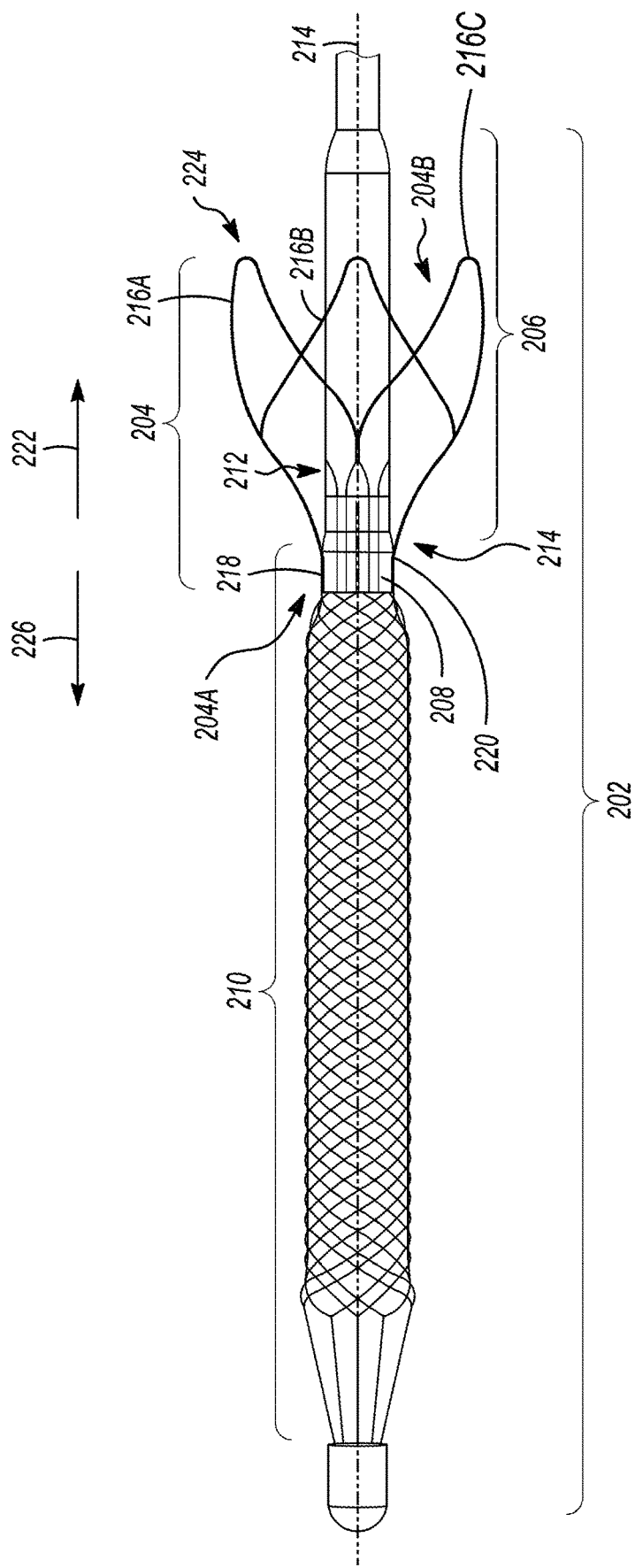
FIG. 3 depicts a side view of a circulatory support device having an exemplary anchoring device, in accordance with embodiments of the subject matter disclosed herein.

FIG. 3 depicts a side view of an illustrative circulatory support device 202 having an anchoring device 204, in accordance with embodiments of the subject matter disclosed herein. According to embodiments, the circulatory support device 202 may be, or be similar to, the circulatory support device 102 depicted in FIG. 1. Additionally, or alternatively, the anchoring device 204 may be or be similar to, the anchoring device 104 depicted in FIG. 1.

According to embodiments, the circulatory support device 202 may be a ventricular assist device configured to pump blood from a left ventricle (e.g., the left ventricle 108) of a subject into the subject's aorta (e.g., the aorta 106). In embodiments, the circulatory support device 202 may be used to facilitate pumping blood from some other aspect of the subject's heart and/or vasculature into an adjacent portion of the heart and/or vasculature. As shown in FIG. 3, the circulatory support device 202 includes a blood pump assembly 206 having a distal end 208 at least partially surrounded by a flexible inlet tube 210. A number of blood flow outlet apertures 212 are disposed in a pump assembly 206 proximal to the flexible inlet tube 208. Similar to the embodiment depicted in FIG. 2, a distal portion 204A of the anchoring device 204 may be coupled to the pump assembly 206 either before, during, or after implantation of the circulatory support device 202.

In embodiments, the anchoring device 204 also includes a proximal portion 204B that extends proximally and radially outward from a longitudinal, central axis 214. In the illustrated embodiment, the proximal portion 204B includes a plurality of proximal portions 216A, 216B, 216C. Each proximal portion 216A-216C forms a loop. For example, each proximal portion 216A-216C may include a first end 218 and a second end 220, each of which are coupled to the pump assembly 206. In embodiments, the first and second ends 218, 220 may form an annulus through which the pump assembly 306 is inserted. Between the first and second ends 218, 220, the proximal portions 216A-216C extend in a proximal direction 222. After extending in a proximal direction 222 for a distance, each proximal portion 216A-216C reaches a distal end 224, then loops back and extends in a distal direction 226 back to the first and second ends 220, 222. In embodiments, the distal ends 224 may include barbs for securing the anchoring device 204 to the aorta. In embodiments, the proximal portions 216A-216C may form a basket structure. In embodiments, the proximal portions 216A-216C may overlap or they may not overlap.

In embodiments, the proximal portions 216A-216C may be delivered in a constrained state by, for example, a constraining member (not shown). The constraining member be a sleeve, a sheath, a catheter, and/or the like. Exemplary constraining members are described in more detail below in relation to FIGS. 7A-13B. The constraining member may be removed from the anchoring device 204 so the anchoring device 204 can circumferentially expand to an unconstrained state (as shown) in order to fix the circulatory support device 202 in an exemplary position, as described above. In embodiments, the proximal portions 216A-216C may be equidistant from the central axis 214.

The illustration shown in FIG. 3 is not intended to suggest any limitation as to the scope of use or functionality of embodiments of the present disclosure. The illustration also should not be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure.

Figure 4A:
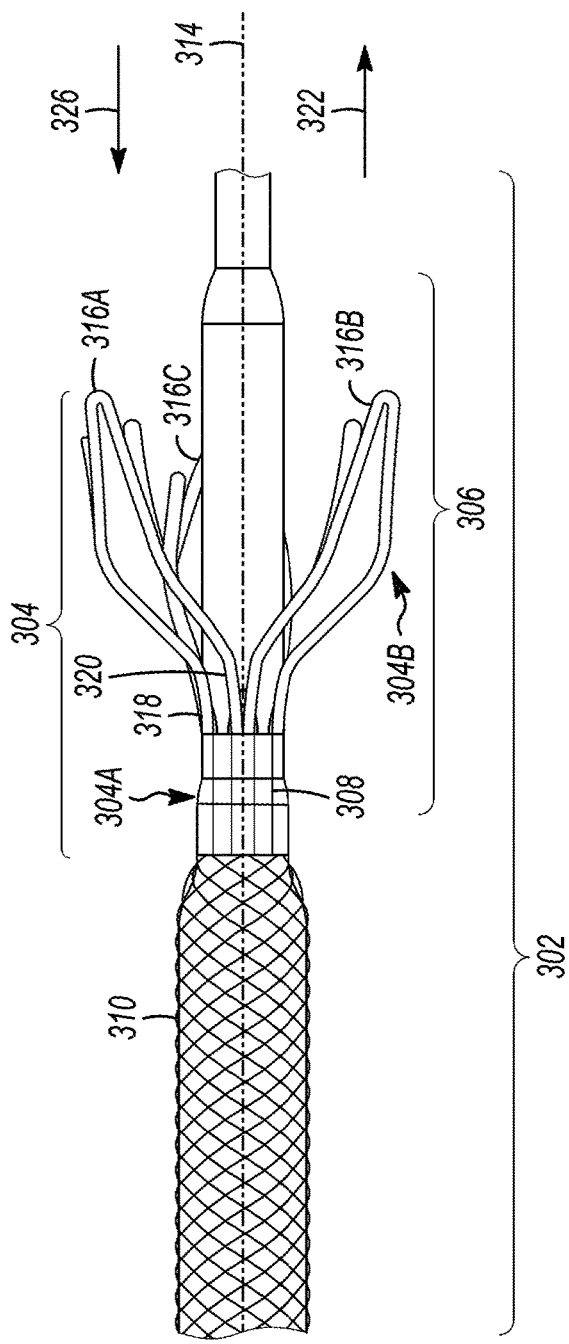
FIG. 4A depicts a side view of a portion of a circulatory support device having another exemplary anchoring device, in accordance with embodiments of the subject matter disclosed herein.
Figure 4B:
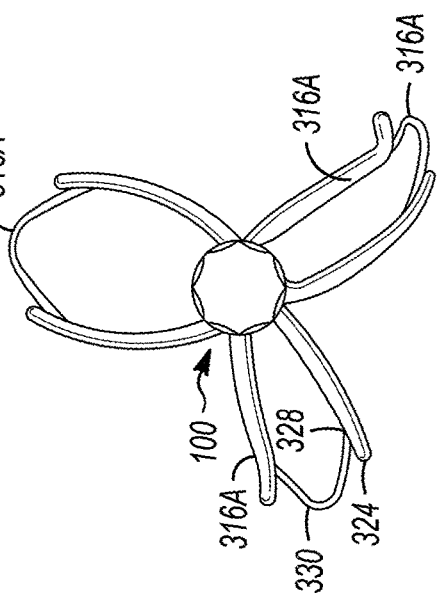
FIG. 4B depicts an end view of the circulatory support device of FIG. 4A, in accordance with embodiments of the subject matter disclosed herein.

FIG. 4A depicts a side view of a portion of a circulatory support device 302 having another exemplary anchoring device 304, in accordance with embodiments of the subject matter disclosed herein. FIG. 4B depicts an end view of the circulatory support device of FIG. 4A, in accordance with embodiments of the subject matter disclosed herein. According to embodiments, the circulatory support device 302 may be, or be similar to, the circulatory support device 102 depicted in FIG. 1 and/or the circulatory support device 202 depicted in FIG. 3. Additionally, or alternatively, the anchoring device 304 may be or be similar to, the anchoring device 104 depicted in FIG. 1 and/or the anchoring device 204 depicted in FIG. 3.

According to embodiments, the circulatory support device 302 may be a ventricular assist device configured to pump blood from a left ventricle (e.g., the left ventricle 108) of a subject into the subject's aorta (e.g., the aorta 106). In embodiments, the circulatory support device 302 may be used to facilitate pumping blood from some other aspect of the subject's heart and/or vasculature into an adjacent portion of the heart and/or vasculature. As shown in FIG. 4A, the circulatory support device 302 includes a blood pump assembly 306 having a distal end 308 at least partially surrounded by a flexible inlet tube 310. Similar to the embodiment depicted in FIG. 3, a distal portion 304A of the anchoring device 304 may be coupled to the pump assembly 306 either before, during, or after implantation of the circulatory support device 302. In embodiments, the anchoring device 304 also includes a proximal portion 304B that extends proximally and radially outward from a longitudinal, central axis 314. In the illustrated embodiment, the proximal portion 304B includes a plurality of proximal portions 316A, 316B, 316C. Each proximal portion 316A-316C forms a loop. For example, each proximal portion 316A-316C may include a first end 318 and a second end 320, each of which are coupled to the pump assembly 306. In embodiments, the first and second ends 318, 320 may form an annulus through which the pump assembly 306 is inserted. Between the first and second ends 318, 320, the proximal portions 316A-316C extend in a proximal direction 322. After extending in a proximal direction 322 for a first distance, each proximal portion 316A-316C reaches a first intermediate point 324, then extends in a distal direction 326 for a second distance that is shorter than the first distance. After extending in a proximal direction 322 for the second distance, each proximal portion 316A-316C reaches a second intermediate point 328, then extends in a proximal direction for a third distance. The third distance may be approximately equal to the second distance. After extending in a proximal direction 322 for the third distance, each proximal portion 316A-316C reaches a distal end 330. Then each proximal portion 316A-316C extends in a distal direction 326 for the third distance then back in a proximal direction 322 for the second distance and then back in a distal direction 326 for the first distance to the second end 322. In embodiments, the distal ends 324 may include barbs for securing the anchoring device 304 to the aorta. In embodiments, the proximal portions 316A-316C may form a basket structure. In embodiments, the proximal portions 316A-316C may overlap or they may not overlap.

In embodiments, the proximal portions 316A-316C may be delivered in a constrained state by, for example, a constraining member (not shown). The constraining member be a sleeve, a sheath, a catheter, and/or the like. Exemplary constraining members are described in more detail below in relation to FIGS. 7A-13B. The constraining member may be removed from the anchoring device 304 so the anchoring device 304 can circumferentially expand to an unconstrained state (as shown) in order to fix the circulatory support device 302 in an exemplary position, as described above. In embodiments, the proximal portions 316A-316B may be equidistant from the central axis 314.

The illustration shown in FIGS. 4A-4B is not intended to suggest any limitation as to the scope of use or functionality of embodiments of the present disclosure. The illustration also should not be interpreted as having any dependency or requirement related to any single component or combination of components illustrated therein. Additionally, various components depicted in 4A-4B may be, in embodiments, integrated with various ones of the other components depicted therein (and/or components not illustrated), all of which are considered to be within the ambit of the present disclosure.

Figure 5B:
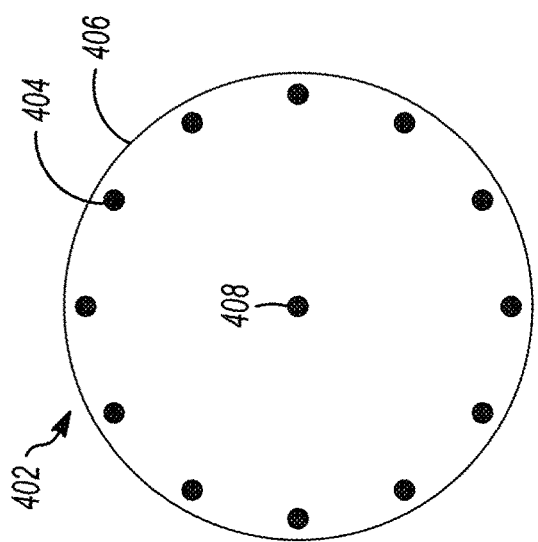
FIGS. 5A and 5B depict a conceptual end view of another exemplary anchoring device, in accordance with embodiments of the subject matter disclosed herein.
Figure 5A:
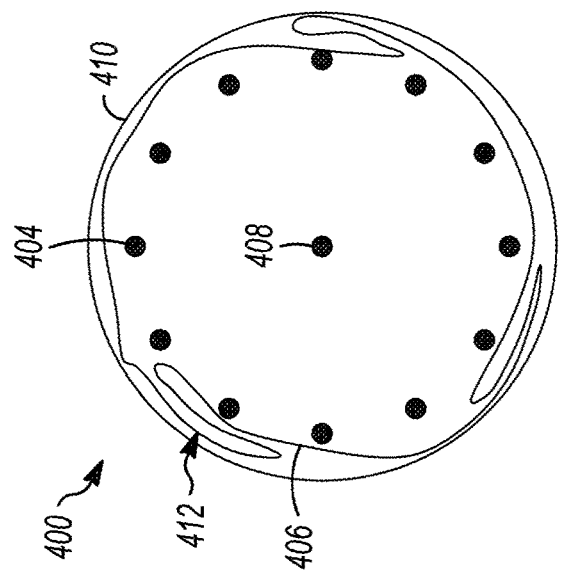

FIGS. 5A and 5B depict a conceptual end view of another exemplary anchoring device 400, in accordance with embodiments of the subject matter disclosed herein. More specifically, FIG. 5A depicts a conceptual end view of another exemplary anchoring device 400 in a constrained configuration and FIG. 5B depicts a conceptual end view of the exemplary anchoring device 400 depicted in FIG. 5A in an unconstrained configuration. According to embodiments, the anchoring device 400 may be or be similar to, the anchoring device 104 depicted in FIG. 1, the anchoring device 204 depicted in FIG. 3, and/or the anchoring device 304 depicted in FIG. 4.

In the illustrated embodiment, the anchoring device 400 has a proximal portion 402 including plurality of elongate members 404 surrounded by a membrane 406. In embodiments, the elongate members 404 and membrane 406 are centered about a central axis 408. When in a constrained configuration, the proximal portions 404 and the membrane 406 are constrained by a constraining member 410. In embodiments, the constraining member 408 may be a sleeve, a sheath, a catheter, and/or the like. In embodiments, the membrane 406 includes overlapping portions 412 that overlap when the anchoring device 400 is in a constrained configuration, as illustrated in FIG. 5A. However, when the constraining member 410 is removed from the proximal portion 402, the elongate members 402 and surrounding membrane 406 circumferentially expand about the central axis to an unconstrained configuration, as illustrated in FIG. 5B. In the unconstrained configuration, the membrane 406 may no longer include overlapping portions 412. In embodiments, the outer edges of the membrane 406 may be equidistant from the central axis 314.

FIGS. 5A and 5B depict a conceptual cross-sectional view of a circulatory support device having another exemplary anchoring device, in accordance with embodiments of the subject matter disclosed herein. Another embodiment consists of a sheathed frame that is folded on itself. When unsheathed, it opposes the aortic walls. This design functions like a folded balloon on a balloon catheter. This could be a selectively deployable anchoring device as well as a non-selectively deployable device dependent on the introducer sheath that is used. The sheathed frame would need to be resilient enough to survive folding upon itself over the canula of the device and fold easily back onto the surface of the cannula when being recaptured for removal.

Figure 6:
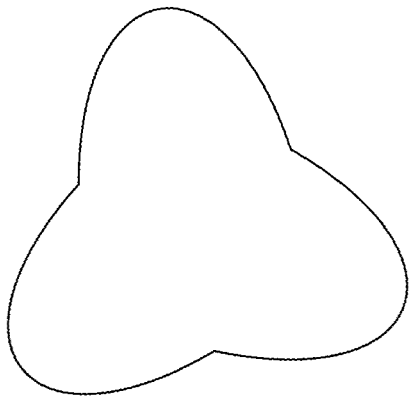
FIG. 6 depicts a conceptual cross-sectional delivery catheter, in accordance with embodiments of the subject matter disclosed herein.

FIG. 6 depicts a conceptual cross-sectional delivery catheter 500, in accordance with embodiments of the subject matter disclosed herein. As set forth above, the anchoring devices 104, 204, 304, 400 may be arranged over a circulatory support device via a delivery catheter. In embodiments, the delivery catheter 500 could have a tricuspid cross-sectional shape, as illustrated in FIG. 6. In embodiments, the tricuspid shape could mimic the shape of the aortic valve (e.g., the aortic valve 114). This shape could allow for improved leaflet coaptation against the aortic valve itself. Additionally, or alternatively, this shape may facilitate centering of the anchoring device 104, 204, 304, 400 to reduce the likelihood of aortic regurgitation.

FIGS. 7A and 7B are schematic diagrams depicting operation of an exemplary anchoring deployment mechanism 600, in accordance with embodiments of the subject matter disclosed herein. In the illustrated embodiment, the anchoring device 502 is arranged within a catheter 504. In embodiments, the anchoring device 502 may be, or be similar to, the anchoring device 104 depicted in FIG. 1, the anchoring device 204 depicted in FIG. 3, the anchoring device 304 depicted in FIG. 4, and/or the anchoring device 400 depicted in FIG. 5.

In embodiments, the catheter 504 includes openings 506 through which the anchoring device 502 protrudes. In embodiments, a distal end 502A of the anchoring device 502 is coupled to a distal end 508 of the catheter 504. Additionally, or alternatively, an actuation member 510 may be attached to a proximal end 502B of the anchoring device 502. In the illustrated embodiment, the actuation member 510 is a push-pull rod. In a constrained configuration, the actuation member 510 is arranged along a proximal position, as illustrated in FIG. 7B. To actuate the anchoring device 502, the actuation member 510 is biased in a distal direction towards the distal end 508 of the catheter 504 to a distal position, as illustrated in FIG. 7A. Once in the distal position, the anchoring device 502 projects out of the openings 506 and circumferentially expands to an expanded configuration, as illustrated in FIG. 7A.

Figure 8A:
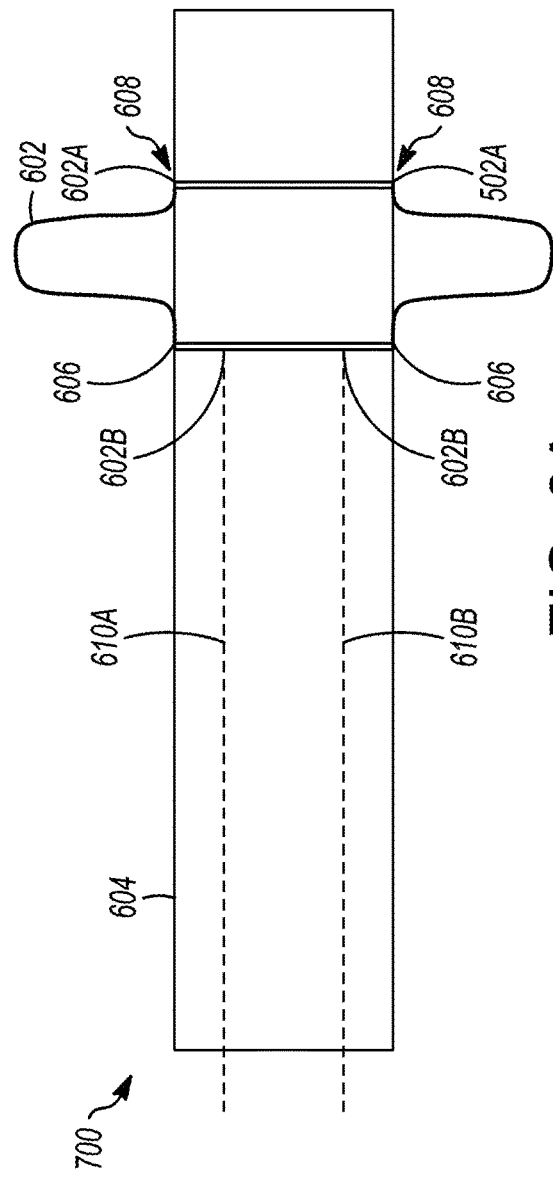
FIGS. 8A and 8B are schematic diagrams depicting operation of another exemplary anchoring deployment mechanism, in accordance with embodiments of the subject matter disclosed herein.
Figure 8B:
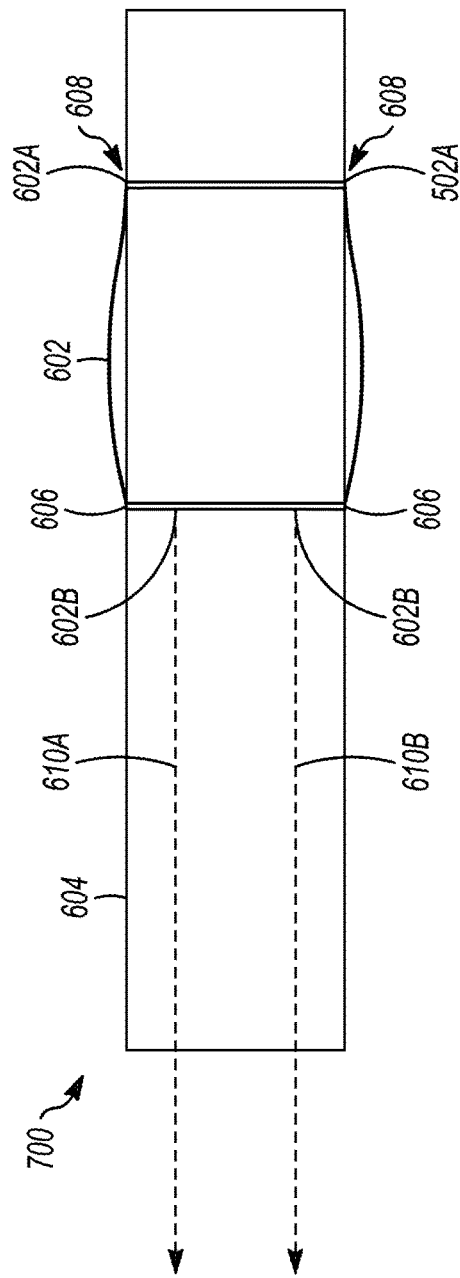

FIGS. 8A and 8B are schematic diagrams depicting operation of an exemplary anchoring deployment mechanism 700, in accordance with embodiments of the subject matter disclosed herein. In the illustrated embodiment, the anchoring device 602 is arranged within a catheter 604. In embodiments, the anchoring device 602 may be, or be similar to, the anchoring device 104 depicted in FIG. 1, the anchoring device 204 depicted in FIG. 3, the anchoring device 304 depicted in FIG. 4, and/or the anchoring device 400 depicted in FIG. 5.

In embodiments, the catheter 604 includes openings 606 through which the anchoring device 602 protrudes. In embodiments, a distal end 602A of the anchoring device 602 is coupled to a distal end 608 of the catheter 604. Additionally, or alternatively, an actuation member 610 may be attached to a proximal end 602B of the anchoring device 602. In the illustrated embodiment, the actuation member 610 are push-pull wires 610. In a constrained configuration, the actuation member 610 is arranged along a proximal position, as illustrated in FIG. 8B. To actuate the anchoring device 602, the actuation member 610 is biased in a distal direction towards the distal end 608 of the catheter 604 to a distal position, as illustrated in FIG. 8A. Once in the distal position, the anchoring device 602 projects out of the openings 606, as illustrated in FIG. 8A.

FIGS. 9A and 9B are schematic diagrams depicting operation of another exemplary anchoring deployment mechanism 800, in accordance with embodiments of the subject matter disclosed herein. In the illustrated embodiment, the anchoring device 702 is arranged within a catheter 704. In embodiments, the anchoring device 702 may be, or be similar to, the anchoring device 104 depicted in FIG. 1, the anchoring device 204 depicted in FIG. 3, the anchoring device 304 depicted in FIG. 4, and/or the anchoring device 400 depicted in FIG. 5.

In embodiments, the catheter 704 includes openings 706 through which the anchoring device 702 protrudes. In embodiments, an actuation member 708 may be attached to the anchoring device 702. In the illustrated embodiment, the actuation member 708 is a push-pull rod. In a constrained configuration, the actuation member 708 is arranged in a distal position, as illustrated in FIG. 9B. To actuate the anchoring device 702, the actuation member 708 is biased in a proximal direction to a distal position, as illustrated in FIG. 9A. Once in the proximal position, the anchoring device 702 projects out of the openings 706, as illustrated in FIG. 9A.

FIGS. 10A and 10B are schematic diagrams depicting operation of another exemplary anchoring deployment mechanism 900, in accordance with embodiments of the subject matter disclosed herein. In the illustrated embodiment, the anchoring device 802 is arranged within a catheter 804. In embodiments, the anchoring device 802 may be, or be similar to, the anchoring device 104 depicted in FIG. 1, the anchoring device 204 depicted in FIG. 3, the anchoring device 304 depicted in FIG. 4, and/or the anchoring device 400 depicted in FIG. 5.

In embodiments, the catheter 804 includes openings 806 through which the anchoring device 802 protrudes. In embodiments, the openings 806 may include cut-outs so the anchoring device 802 is entirely contained within the catheter 804. In embodiments, an actuation member 808 may be attached to the anchoring device 802. In the illustrated embodiment, the actuation member 808 is a push-pull rod. In a constrained configuration, the actuation member 808 is arranged in a distal position, as illustrated in FIG. 10B. To actuate the anchoring device 802, the actuation member 808 is biased in a proximal direction to a distal position, as illustrated in FIG. 10A. Once in the proximal position, the anchoring device 802 projects out of the openings 806, as illustrated in FIG. 10A.

FIGS. 11A and 11B are schematic diagrams depicting operation of another exemplary anchoring deployment mechanism 1000, in accordance with embodiments of the subject matter disclosed herein. In the illustrated embodiment, the anchoring device 902 is arranged on an exterior of a catheter 904. In embodiments, the anchoring device 902 may be, or be similar to, the anchoring device 104 depicted in FIG. 1, the anchoring device 204 depicted in FIG. 3, the anchoring device 304 depicted in FIG. 4, and/or the anchoring device 400 depicted in FIG. 5.

In embodiments, the catheter 904 includes a constraining member 906 arranged around the catheter 904. In embodiments, an actuation member 908 may be attached to the constraining member 906. In the illustrated embodiment, the actuation member 908 is a pulley system. In a constrained configuration, the constraining member 906 is arranged in a proximal position, as illustrated in FIG. 10B. In the proximal position, the constraining member 906 is arranged around the anchoring device 902 and holds the anchoring device 902 against the exterior of the catheter 904. To actuate the anchoring device 902, the actuation member 908 is actuated to move the constraining member 906 in a distal direction to a distal position, as illustrated in FIG. 11A. Once in the distal position, the anchoring device 902 is no longer constrained against the exterior of the catheter 904 so the anchoring device 902 projects outward from the sides of the catheter 904.

Figure 12A:
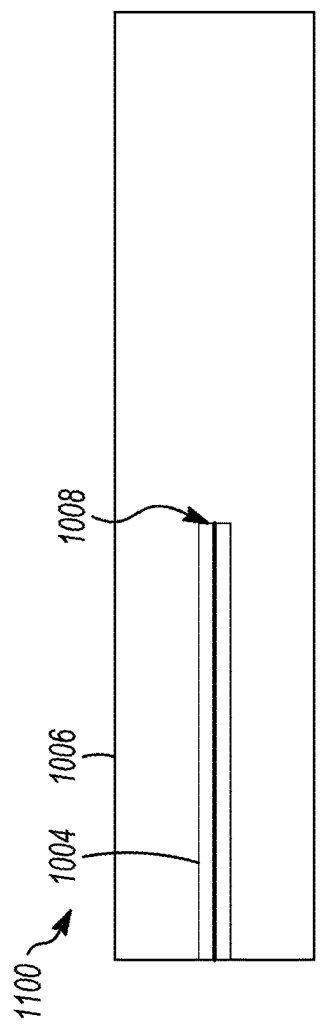
FIGS. 12A-12C are schematic diagrams depicting operation of another exemplary anchoring deployment mechanism, in accordance with embodiments of the subject matter disclosed herein.
Figure 12B:
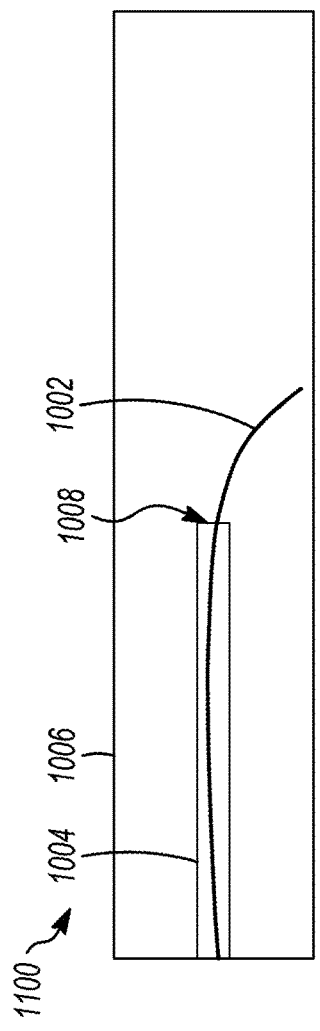
Figure 12C:
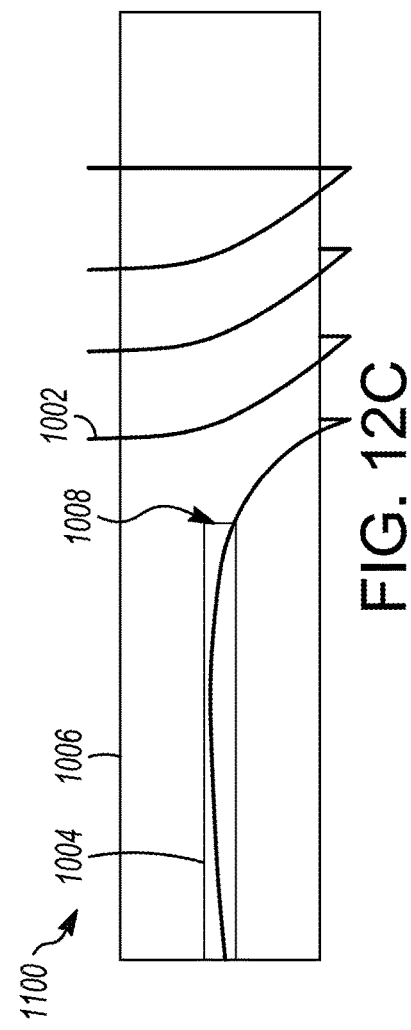

FIGS. 12A-12C are schematic diagrams depicting operation of another exemplary anchoring deployment mechanism 1100, in accordance with embodiments of the subject matter disclosed herein. In the illustrated embodiment, the anchoring device 1002 is arranged within a constraining member 1004. In embodiments, the anchoring device 1002 may be, or be similar to, the anchoring device 104 depicted in FIG. 1, the anchoring device 204 depicted in FIG. 3, the anchoring device 304 depicted in FIG. 4, and/or the anchoring device 400 depicted in FIG. 5.

In embodiments, the constraining member 1004 may be arranged on an exterior of a catheter 1006. In a constrained configuration, the constraining member 1004 is arranged in a distal position, as illustrated in FIG. 12A. In the distal position, the constraining member 1006 constrains the anchoring device 1002 longitudinally, as illustrated in FIG. 12A. To actuate the anchoring device 1002, the constraining member 1004 is moved in a proximal direction. As the constraining member 1004 is moved in a proximal direction the anchoring device 1002 is no longer constrained and projects out of a distal end 1008 of the constraining member 1004, as illustrated in FIGS. 12B and 12C. After projecting out of the distal end 1008 of the constraining member 1004, the anchoring device 1002 assumes its predefined shape which is a helix that surrounds the catheter 1006, as illustrated in FIG. 12C.

Figure 13A:
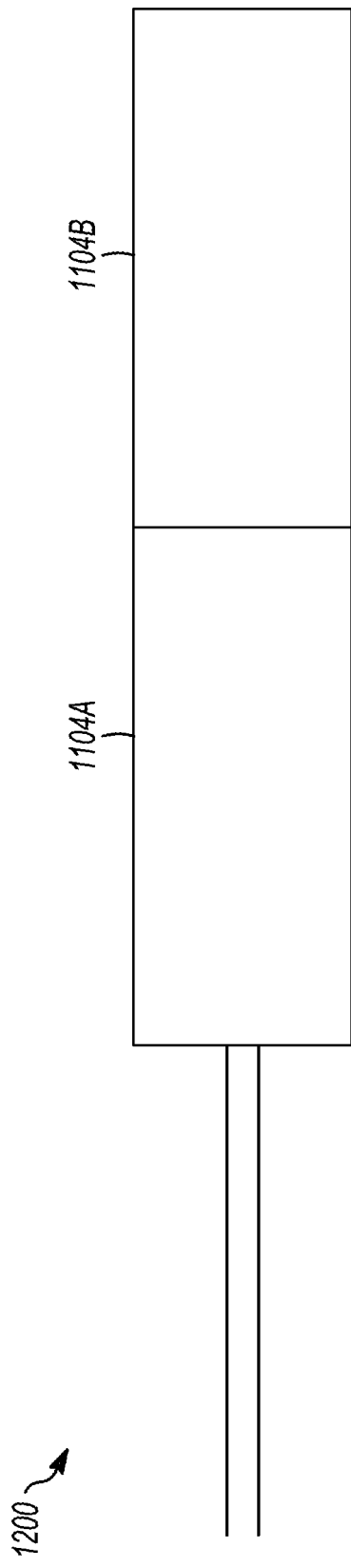
FIGS. 13A and 13B are schematic diagrams depicting operation of another exemplary anchoring deployment mechanism, in accordance with embodiments of the subject matter disclosed herein.
Figure 13B:
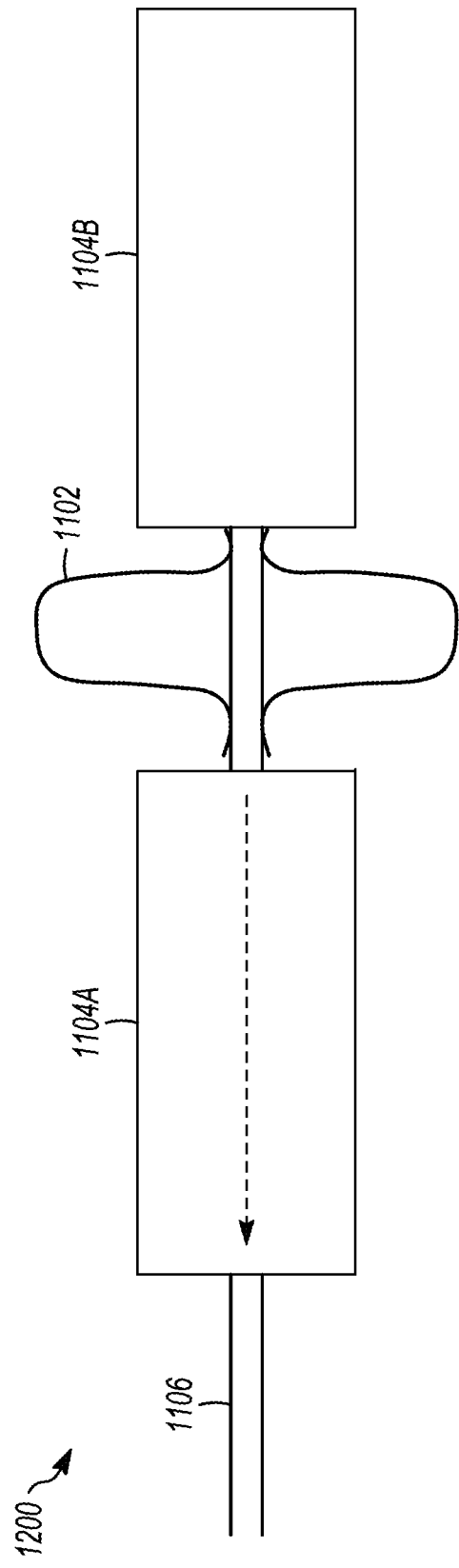

FIGS. 13A and 13B are schematic diagrams depicting operation of another exemplary anchoring deployment mechanism 1200, in accordance with embodiments of the subject matter disclosed herein. In the illustrated embodiment, the anchoring device 1102 is arranged on an interior a catheter 1104. In embodiments, the anchoring device 1102 may be, or be similar to, the anchoring device 104 depicted in FIG. 1, the anchoring device 204 depicted in FIG. 3, the anchoring device 304 depicted in FIG. 4, and/or the anchoring device 400 depicted in FIG. 5.

In embodiments, the catheter 1104 includes a proximal portion 1104A and a distal portion 1104B. In embodiments, an actuation member 1106 may be attached to the proximal portion 1104A. In the illustrated embodiment, the actuation member 1106 is an electrical wire. In a constrained configuration, the proximal portion 1104A abuts the distal portion 1104B, as illustrated in FIG. 13A. In the constrained configuration, the catheter 1104 constrains the anchoring device 1102 within an interior of the catheter 1104. To actuate the anchoring device 1102, the actuation member 1106 is actuated to move the proximal portion 1104A in a proximal direction to a proximal position, as illustrated in FIG. 13B. Once the proximal portion 1104A is in the proximal position, the anchoring device 1102 is no longer constrained within an interior of the catheter 1104 so the anchoring device 1102 projects outward.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. An apparatus, comprising:
a cardiac pump comprising a cannula configured to draw blood from a left ventricle of a heart of a subject into an inflow distal section of the cardiac pump, and the cardiac pump configured to release the blood into the aorta of the subject from a plurality of outflow windows in an outflow proximal section of the cardiac pump;
an expandable anchoring device extending along a longitudinal axis, wherein the expandable anchoring device is arranged about a central axis, wherein a distal portion of the expandable anchoring device defines an annulus through which the cardiac pump can be arranged and to which a proximal region of the cardiac pump can be coupled, and wherein a proximal portion of the expandable anchoring device has a conical shape and is configured to circumferentially expand to an unconstrained configuration that has a cross-sectional diameter greater than a diameter of the annulus and thereby engages an inner circumference of the aorta; and
a constraining member arranged over the expandable anchoring device to constrain the expandable anchoring device in a constrained configuration for delivery of the expandable anchoring device;
wherein when the expandable anchoring device is coupled to the cardiac pump and expanded within the aorta, the plurality of outflow windows are positioned distal and upstream of the proximal portion of the expandable anchoring device that is engaged with the inner circumference of the aorta.

2. The apparatus of claim 1, wherein the proximal portion comprises a plurality of proximal portions that are configured to expand equidistant from the central axis when in the unconstrained configuration and engage the aortic wall.

3. The apparatus of claim 2, wherein the plurality of proximal portions comprise a plurality of separate, elongate members configured to engage the aortic wall.

4. The apparatus of claim 3, wherein the plurality of separate, elongate members are barbs configured to engage the aortic wall.

5. The apparatus of claim 2, wherein the plurality of proximal portions comprises a plurality of loop elements.

6. The apparatus of claim 1, wherein the distal portion includes an elongate member that is secured to a coupling loop of the cardiac pump via an interference fit.

7. An apparatus comprising:
a cardiac pump comprising a cannula configured to draw blood from a left ventricle of a heart of a subject into an inflow distal section of the cardiac pump, and the cardiac pump configured to release the blood into the aorta of the subject from a plurality of outflow windows in an outflow proximal section of the cardiac pump;
an expandable anchoring device extending along a longitudinal axis, wherein the expandable anchoring device is arranged about a central axis, wherein a distal portion of the expandable anchoring device defines an annulus through which the cardiac pump can be arranged and to which a proximal region of the cardiac pump can be coupled, and wherein a proximal portion of the expandable anchoring device is configured to circumferentially expand to an unconstrained configuration that has a cross-sectional diameter greater than a diameter of the annulus and thereby engages an inner circumference of the aorta; and
a constraining member arranged over the expandable anchoring device to constrain the expandable anchoring device in a constrained configuration for delivery of the expandable anchoring device;
wherein when the expandable anchoring device is coupled to the cardiac pump and expanded within the aorta, the plurality of outflow windows are positioned distal and upstream of the proximal portion of the expandable anchoring device that is engaged with the inner circumference of the aorta;
wherein the proximal portion of the expandable anchoring device comprises a membrane, the membrane comprising portions that are overlapping when in the constrained configuration and are non-overlapping when in the unconstrained configuration.

8. The apparatus of claim 1, further comprising a delivery catheter, wherein the delivery catheter has a tricuspid cross-sectional shape, and wherein the expandable anchoring device is arranged over the delivery catheter during delivery of the expandable anchoring device.

9. The apparatus of claim 1, wherein the expandable anchoring device is formed from nitinol.

10. An apparatus, comprising:
a cardiac pump comprising a cannula configured to draw blood from a left ventricle of a heart of a subject, and the cardiac pump configured to release the blood into the aorta of the subject;
an expandable anchoring device extending along a longitudinal axis, wherein the expandable anchoring device is arranged about a central axis, wherein a distal portion of the expandable anchoring device defines an annulus through which the cardiac pump can be arranged and to which a proximal region of the cardiac pump can be coupled, and wherein a proximal portion of the expandable anchoring device is configured to circumferentially expand to an unconstrained configuration that has a cross-sectional diameter greater than a diameter of the annulus and thereby engages an inner circumference of the aorta; and
a constraining member arranged over the expandable anchoring device to constrain the expandable anchoring device in a constrained configuration for delivery of the expandable anchoring device;
wherein the cardiac pump is configured to be placed within the heart of the subject before delivery of the expandable anchoring device within the aorta and coupling of the expandable anchoring device to the cardiac pump;
wherein the proximal portion comprises a plurality of proximal portions that are configured to expand equidistant from the central axis when in the unconstrained configuration and engage the aortic wall, wherein the plurality of proximal portions comprises a plurality of loop elements.

11. The apparatus of claim 10, wherein the plurality of loop elements comprise a plurality of separate, elongate loop elements configured to engage the aortic wall.

12. The apparatus of claim 11, wherein the plurality of separate, elongate loop elements include barbs configured to engage the aortic wall.

13. The apparatus of claim 10, wherein the distal portion includes an elongate member that is secured to a coupling loop of the cardiac pump via an interference fit.

14. The apparatus of claim 10, wherein the proximal portion of the expandable anchoring device comprises a membrane, the membrane comprising portions that are overlapping when in the constrained configuration and are non-overlapping when in the unconstrained configuration.

15. The apparatus of claim 10, further comprising a delivery catheter, wherein the delivery catheter has a tricuspid cross-sectional shape, and wherein the expandable anchoring device is arranged over the delivery catheter during delivery of the expandable anchoring device.

* * * * *